United States Patent [19]

Beuther et al.

[11] 4,102,914

[45] Jul. 25, 1978

[54] PROCESS FOR PREPARING ACRYLONITRILE

[75] Inventors: Harold Beuther, Gibsonia; Robert A. Innes, Pittsburgh; Harold E. Swift, Gibsonia, all of Pa.

[73] Assignee: Gulf Research & Development Company, Pittsburgh, Pa.

[21] Appl. No.: 798,755

[22] Filed: May 20, 1977

[51] Int. Cl.² ........................................... C07C 120/14
[52] U.S. Cl. ................................................. 260/465.3
[58] Field of Search ..................................... 260/465.3

[56] References Cited

U.S. PATENT DOCUMENTS

| | | |
|---|---|---|
| 3,472,892 | 10/1969 | Callahan et al. .................. 260/465.3 |
| 3,546,268 | 12/1970 | Ikeda et al. ....................... 260/465.3 |
| 3,639,103 | 2/1972 | Sheely ........................... 260/465.3 X |
| 3,819,679 | 6/1974 | Sheely ............................... 260/465.3 |
| 3,960,925 | 6/1976 | Gasson et al. ..................... 260/465.3 |

*Primary Examiner*—Joseph Paul Brust

[57] ABSTRACT

A process for preparing acrylonitrile which comprises passing a gaseous mixture comprising propylene, ammonia and molecular oxygen and an ammoxidation catalyst through a reaction zone while controlling the superficial linear gas velocity and solids feeds rate to achieve a state of fast fluidization.

17 Claims, 1 Drawing Figure

PROCESS FOR PREPARING ACRYLONITRILE

BACKGROUND OF THE INVENTION

1. Field of Invention

This invention relates to a process whereby high conversions to acrylonitrile can be obtained at unusually high weight hourly space velocities. More particularly, it relates to a process wherein an entrained ammoxidation catalyst and a gaseous mixture comprising propylene, ammonia, and oxygen are passed through a reaction zone while controlling the superficial linear gas velocity and solids feed rate to achieve a state of fast fluidization.

2. Description of the Prior Art

Acrylonitrile can be prepared by passing a gaseous mixture comprising propylene, ammonia and air over a mixed-oxide catalyst at a temperature between 375° C and 525° C. The reaction is highly exothermic. In a few cases manufacturers have used a multitubular fixed-bed reactor cooled by molten salts; but, usually, a fluidized bed reactor is preferred to facilitate heat removal and maintain a uniform reaction temperature. U.S. Pat. No. Re. 27,718 to Sennewald, et al and U.S. Pat. Nos. 3,230,246, 3,427,343 and 3,472,892 to Callahan et al are illustrative of the state of the art in fluidized-bed reactor design and operation, as applied to propylene ammoxidation.

In the fluidized bed processes of the prior art, the reactant gases are passed upward through a bed of suitably-sized catalyst particles at a velocity sufficiently high to buoy the particles and impact to them a violently turbulent fluid-like motion, but not so high as to sweep the bed out of the reactor. A stable bed is maintained which has a distinct surface resembling a boiling liquid. The carry-over of catalyst particles in the reactor effluent is small. Catalyst particles in the 10 to 150 micron size range are preferred for optimum fluidization. With particles of this size, superficial gas velocities between about 0.5 centimeters per second and about 100 centimeters per second are generally required to achieve a stable fluidized bed.

Though the use of the prior art fluidized bed processes is advantageous from a heat transfer standpoint, it is recognized that there are some inherent disadvantages. For example, it is difficult to achieve complete propylene conversion in a single-stage fluidized bed reactor because a certain amount of the gas residing in the rising bubbles tends to pass through the bed without contacting the catalyst. Furthermore, the back-mixing of reactant and product gases is appreciable and encourages secondary reactions which reduce the selectivity for acrylonitrile. A multi-stage reactor such as described in the patents to Callahan et al minimizes these problems, but is more costly to build and operate. A disadvantage of both the single-stage and multi-stage processes is that gas velocities and, thus, throughput, are limited by the need to maintain a stable bed. As a result, the prior art processes are unable to take full advantage of a highactivity catalyst, such as disclosed, for example, in our pending U.S. Pat. Applications Ser. Nos. 645,418 and 645,419, now U.S. Pat. Nos. 4,045,373 and 4,040,983, respectively.

SUMMARY OF THE INVENTION

We have found that excellent yields of acrylonitrile can be obtained at unusually high propylene weight hourly space velocities by passing an entrained ammoxidation catalyst and a gaseous mixture comprising propylene, ammonia and oxygen through a reaction zone while controlling the superficial linear gas velocity and the solids feed rate to achieve a state of fast fluidization.

The process disclosed and claimed herein can be understood by reference to the attached drawings.

In FIG. 1 an oxygen-containing gas, such as air, is introduced by line 2 into one end of a tubular reactor 8 with sufficient velocity to entrain the catalyst particles entering through line 4. Propylene and ammonia are then added by line 6 to initiate the ammoxidation reaction. The reaction continues as the reactants and catalyst proceed through the reactor. The reactor effluent is directed through line 10 to a solids separator 12 where the product gases are taken overhead through line 14 and the catalyst particles are recovered for recycle to the reactor through line 4.

Additional lines can be provided so that the reactant gases can be added in stages. For example, oxygen can be added in stepwise fashion to improve selectivity. Thus a portion of the oxygen needed for reaction is added, along with diluent gases such as nitrogen or steam, via line 2. The catalyst enters via line 4 and is entrained in the gas stream. Propylene and ammonia are then added via line 6 to begin the reaction. The remaining oxygen required for the reaction is added in stepwise fashion via any one or combination of lines 16, 18, 20, 22 and 24, thereby maintaining a low partial pressure of oxygen throughout.

The relative amounts of propylene, ammonia and oxygen introduced to the reaction zone can be varied over a wide range. The molar ratio of oxygen to propylene can range from about 0.5:1 to about 10:1. It is preferred, however, that a slight excess of oxygen be added over that required for reaction. Thus, a preferred range would be about 1.5:1 to about 2.5:1. The molar ratio of ammonia to propylene can range from about 0.5:1 to about 10:1; but, since it is desirable to add just enough ammonia to prevent acrolein formation, a preferred range would be about 0.9:1 to about 1.3:1.

With most catalysts the selectivity for acrylonitrile production decreases with increasing pressure, thus, the reaction pressure will normally range from atmospheric pressure to no more than about 100 pounds per square inch gauge (about 0 to about 7.0 kilograms per square centimeter gauge), preferably about 0 to 50 pounds per square inch gauge (about 0 to about 3.5 kilograms per square centimeter gauge). The reaction temperature can range from about 375° to about 525° C., but is preferably about 450° to about 490° C. The reaction is highly exothermic; therefore, cooling devices must be employed to maintain the reaction temperature within the desired range. For example, small diameter reactors can be immersed in baths containing molten salts or fluidized sand. Larger diameter reactors will usually contain internal heat exchanger tubes to remove heat. The circulating catalyst can also serve as a heat exchange medium. By cooling the catalyst particles recovered from the reactor effluent and returning them to the reactor at a reduced temperature, the temperatures within the reactor can be maintained within the desired limits.

To obtain optimum acrylonitrile yields the superficial linear gas velocity and the solids feed rate must be carefully controlled so that the reactant gases move through the reactor in substantially plug flow while the catalyst particles move as an entrained dense suspension characterized by extreme turbulence and substantial backmixing. This condition has been dubbed fast fluidization by Joseph Yerushalmi, et al (Ind. Eng. Chem. Process Des. Dev., Vol 15, No. 1, 1976).

To achieve fast fluidization a superficial linear gas velocity of at least about 1.5 meters per second, but, preferably, at least about 2.0 meters per second is required. The superficial linear gas velocity should not exceed about 7.5 meters per second and will preferably be less than about 4.5 meters per second. The superficial linear gas velocity is calculated by dividing the volumetric flow rate of the feed gases at reaction conditions by the cross-sectional area of the reactor. The solids feed rate must be adjusted to achieve a solids density between about 16 to about 240 kilograms per cubic meter, preferably about 80 to about 200 kilograms per cubic meter. The solids density is defined as the total weight of catalyst in the reaction zone divided by the volume of the reaction zone. The solids feed rate required to achieve appropriate solids density will depend on the size and shape of the reactor and will range from about 5 to about 250 kilograms per square meter per second.

The residence time of the reactant gases, defined as the length of the reaction zone divided by the superficial linear gas velocity, is suitably from about 0.1 to about 20 seconds and is preferably less than about 10 seconds but greater than about one second. A highly active catalyst is required for the process. Any catalyst capable of producing acrylonitrile at a rate of at least about 0.1 gram of acrylonitrile per gram of catalyst per hour can be employed. Suitable catalysts include, for example, those defined by the formula $USb_2MO_{9-10}$, where M = Sn, Ti, Zr or Hf as claimed in U.S. said Applications Ser. Nos. 645,419 and 645,418 to Innes et al. In order to make these catalysts sufficiently attrition resistant for use in the present process, it is preferred that they be combined with a suitable support or binder, such as silica.

To minimize product degradation it is critical that the reaction be terminated as soon as the desired propylene conversion is achieved. Thus, the mixture of gases and solids is removed from reactor 8 by transfer line 10 and is immediately introduced into separator 12. By "immediately" we mean a time interval of, for example, less than about 1 second, preferably less than about 0.1 second. If desired, the effluent from reactor 8 can be discharged directly into separator 12 with little or no transfer line 10.

To minimize acrylonitrile degradation and/or polymerization reactions, it is desirable that the temperature in separator 12 be maintained within a specified temperature range, that is, at least about 25° C. below the reaction temperature in reactor 8, preferably at least about 40° C. below reaction temperature. Generally the temperature need not be in excess of about 150° C. below reaction temperature, preferably no lower than about 100° C. below reaction temperature.

Separator 12 may be a large-diameter vessel sufficient to substantially reduce the superficial linear gas velocity of the reaction mixture entering therein so that the solid catalyst particles fall by gravity to its base for return to reactor 8 by line 4. The product gases including the desired acrylonitrile are removed from the upper portion of separator 12 by line 14. The separator 12 is operated in such manner that the residence time of gases therein is, for example, less than about one minute, preferably less than about 10 seconds, but of sufficient duration to effect essentially complete separation, usually at least about 0.05 second, preferably at least about 0.1 second. Such residence time is defined by the volume of the separator in cubic meters divided by flow rate of gases therethrough in cubic meters per second at the temperature and pressure in the separator. The rate of flow of solids in line 4 corresponds to the rate of flow of solid in line 10.

In a preferred embodiment, the lower part of reactor 8 can serve as a regeneration zone. Thus, the recycled catalyst introduced into reactor 8 by line 4 is contacted with molecular oxygen from line 2 prior to the addition of ammonia and propylene.

DESCRIPTION OF PREFERRED EMBODIMENTS

Figure 1:
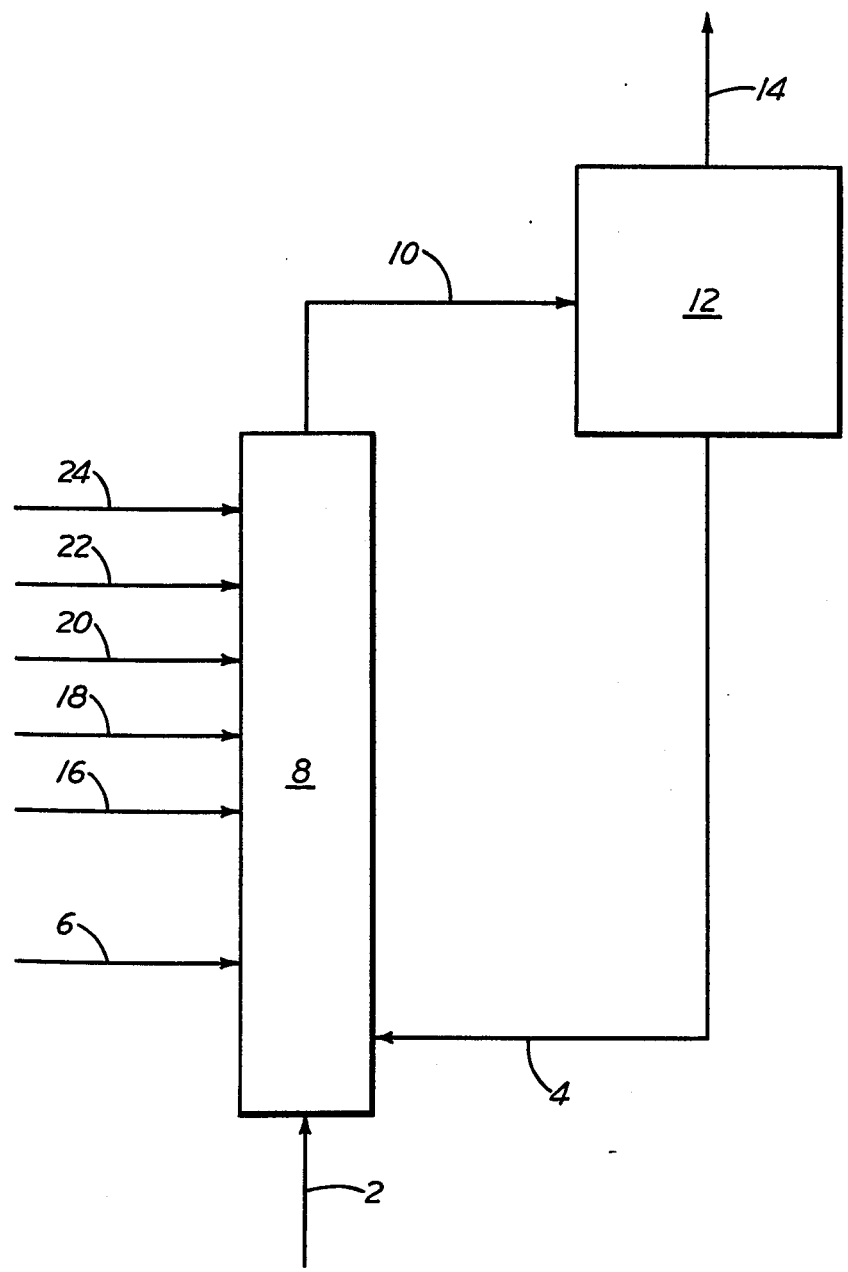

The following will provide a further understanding of the process herein.

A catalyst containing 50 weight percent $USb_2TiO_{9-10}$ and 50 weight percent $SiO_2$ was prepared as follows. Stoichiometric amounts of $UO_2(NO_3)_2.6H_2O$, $TiOSO_4.H_2SO_4.8H_2O$ and $SbCl_3$ were dissolved in hydrochloric acid solution. The hydrous oxides uranium, antimony and titanium were then coprecipitated by addition of concentrated ammonium hydroxide. The precipitate was recovered by filtration and washed with distilled water. The moist filter cake was then mixed with Ludox AS silica sol containing 30 percent $SiO_2$ by weight. Excess water was removed by evaporation and then the resultant slurry was oven dried at 120° C. for 4 hours. The oven-dried material was calcined at 910° C. for 16 hours to crystallize the $USb_2TiO_{9-10}$ phase. The catalyst was ground in a mechanical grinder and sieved to obtain 80-200 mesh (177-74 micron) particles for use in each of the specific runs below.

In Runs Nos. 1 to 4 below, the ammoxidation reactor consisted of two coils of stainless steel tubing (0.64 centimeter outer diameter × 0.48 centimeter inner diameter) immersed in a heated fluidized sand bath. The first coil served as a catalyst preheater, the second as a reaction zone, with the preheater being 6.1 meters in length and the reactor 18.3 meters in length.

Solid catalyst particles were metered into an air stream at a precalibrated rate using a variable speed screw-type feeder. The catalyst particles were entrained in the air stream and carried to the reactor, where they flowed downward through the preheat coil. After propylene and ammonia were added, the flow continued upward through the reaction coil. Each run consisted of a 15-minute off-stream period, during which the equipment was lined out, followed by a 15-minute period during which the product was collected for analysis.

The sand bath temperature was maintained at 470° C., the pressure measured at the inlet to the reactor coil was about 0.175 kilograms per square centimeter gauge. The gaseous feed rates in cubic centimeters per minute at standard temperature and pressure (0° C. and one atmosphere) were as follows: air 1000, ammonia 100 and propylene 90.

The effluent from the reactor was passed immediately into a cylindrical vessel having an inner diameter of 10.2 centimeters and a height of 30.6 centimeters employed as a solids separator. The product gases exited from the solids separator through a sintered stainless steel bayonette filter. The gas residence time in the separator was on the order of 1 minute. At the end of each run the catalyst was recovered from the separator and loaded back into the solids feeder for use in subsequent runs.

The product gases continued through a heated transfer line, maintained at 105° C., to a bubbler which was immersed in a wet ice bath. The bubbler contained 200 milliliters of 0.5N hydrochloric acid which scrubbed ammonia, hydrogen cyanide, acetonitrile and acrylonitrile from the gas stream. The volume of gas exiting from the bubbler was measured with a wet test meter.

One gram of methylethylketone was added to the bubbler solution as an internal standard. A sample of the bubbler solution was then analyzed on a gas chromatograph equipped with a Porapak QS column and a flame ionization detector. Acrylonitrile, acetonitrile, and traces of propylene, and acrolein were compared to the internal standard.

A portion of the bubbler solution was analyzed for HCN. The sample was first made basic by adding 0.5 N NaOH solution until a pH of 12 was obtained. Then the $CN^-$ concentration was measured with a selective ion meter and a cyanide electrode.

Samples of the gas exiting from the bubbler were analyzed by gas chromatography. $O_2$ + Ar, $N_2$ and CO were analyzed on a 5A molecular sieve column. Light gases, $CO_2$, $C_3H_8$, $C_3H_6$, $H_2O$ and traces of acrylonitrile were determined on a Porapak T column.

The approximate solids density was determined independently in a simulated run as follows. The catalyst was metered into an air stream flowing at a rate of 1000 $cm^3$(STP) $min^{-1}$. A 190 $cm^3$(STP) $min^{-1}$ flow of nitrogen was added to the gas stream after the preheat coil to simulate the addition of propylene and ammonia. The temperature in the fluidized sand bath was 470° C. The catalyst exiting from the reactor was collected in a 4-liter vacuum flask positioned on a scale to provide a continuous measurement of catalyst flow. After a steady-state was reached the catalyst holdup in the reactor coils was measured by shutting off the solids feed and weighing the amount of catalyst subsequently eluted. The approximate solids density was calculated by dividing the catalyst holdup by the volume of the coils.

The results obtained are tabulated below in Table I. Selectivity therein is defined as follows:

$$\frac{\text{Moles of product} \times \text{carbon number of product} \times 100}{\text{Moles of propylene converted} \times 3}$$

The yield of acrylonitrile is defined as follows:

$$\frac{\text{Moles of acrylonitrile} \times 100}{\text{Moles of propylene feed}}$$

The approximate weight hourly space velocity (WHSV) is defined as follows:

$$\frac{\text{Weight of propylene feed per hour}}{\text{Approximate solids density} \times \text{volume of the reaction coil}}$$

TABLE I

| Run No. | 1 | 2 | 3 | 4 |
|---|---|---|---|---|
| Solids Feed Rate. Kiolgrams/Square Meter Second | 15.6 | 15.6 | 15.6 | 15.6 |
| Superficial Linear Gas Velocity Meters/Second | 3 | 3 | 3 | 3 |
| Approximate Solids Density, Kilograms/Cubic Meter | 150 | 150 | 150 | 159 |
| Approximate WHSV | 0.2 | 0.2 | 0.2 | 0.2 |
| Separator Temperature, ° C. | 203 | 305 | 403 | 476 |
| Mol Per Cent Propylene Converted | 98.3 | 98.6 | 98.7 | 100 |

TABLE I-continued

| Run No. | 1 | 2 | 3 | 4 |
|---|---|---|---|---|
| Selectivities | | | | |
| CO | 3.1 | 2.8 | 3.0 | 4.2 |
| $CO_2$ | 7.9 | 8.4 | 9.6 | 15.5 |
| HCN | 1.0 | 0.9 | 0.9 | 1.2 |
| Acetontrile | 1.7 | 2.1 | 1.6 | 2.3 |
| Acrylonitrile | 86.0 | 85.3 | 85.0 | 75.8 |
| Yield of Acrylonitrile | 84.5 | 84.1 | 83.9 | 75.8 |

The data in Table I clearly illustrate the advantages of operation in accordance with the process defined and claimed herein. In Runs Nos. 1, 2 and 3 excellent yields of acrylonitrile were obtained at a propylene weight hourly space velocity in excess of those practical in a conventional fluidized bed reactor. This means that the present process enables one to operate with a smaller catalyst inventory than in the conventional fluidized bed reactor. That it is important that the temperature in the separator be maintained within the selected temperature ranges is evident from the data in the table. As long as the separator temperature in Runs Nos. 1, 2 and 3 remained at least about 67° C. below the reactor temperature, conversions and selectivities were maintained at extremely high levels. In Run No. 4 wherein the temperature in the separator was maintained at about the same level as that in the reactor, conversion remained high, but there was a sharp drop in selectivity to acrylonitrile.

Run No. 5

That it is important that the superficial linear gas velocity be at least about 1.5 meters per second, that is, sufficient to entrain solids, maintain them in an agitated stage and continuously remove the same from the reaction zone is apparent from the following. A conventional fluidized bed reactor was constructed from a piece of stainless steel tubing having a length of 28 centimeters, an inner diameter of 2.34 centimeters and an outer diameter of 2.54 centimeters. A porous sintered-stainlesssteel disc was employed as a gas distributor. Another disc was used to prevent catalyst particles from leaving the reactor. The catalyst was the same as that used in Run No. 1. The weight of catalyst, and the pressure, were also the same as that used in Run No. 1. The temperature was maintained at 475° C. While air, ammonia and propylene were used in the same molar ratio as in Run No. 1, the superficial linear gas velocity was 0.13 meters per second. The results obtained are set forth below in Table II.

TABLE II

| Percent Propylene Conversion | 91.2 |
|---|---|
| Selectivities | |
| CO | 2.1 |
| $CO_2$ | 10.3 |
| HCN | 1.3 |
| Acetonitrile | 2.1 |
| Acrylonitrile | 84.2 |
| Yield of Acrylonitrile | 76.8 |

A comparison of the data in Table II with that of Run No. 1 shows that a higher conversion (98.3 percent versus 91.2) and about 10 percent higher yields (84.5 versus 76.8 percent) are obtained when the process is carried out operating within the superficial linear gas velocities required herein.

Obviously, many modifications and variations of the invention, as hereinabove set forth can be made without departing from the spirit and scope thereof, and therefore only such limitations should be imposed as are indicated in the appended claims.

We claim:

1. A process for preparing acrylonitrile which comprises passing a gaseous mixture comprising propylene, ammonia and molecular oxygen and a solid ammoxidation catalyst, said catalyst being a catalyst capable of producing acrylonitrile at a rate of at least about 0.1 gram of acrylonitrile per gram of catalyste per hour, through a reaction zone at an elevated temperature while maintaining a solids density of about 16 to about 240 kilograms per cubic meter and a superficial linear gas velocity of about 1.5 to about 7.5 meters per second wherein the resulting mixture of gases and solids is removed from the reaction zone and is introduced into a separator within a time interval of less than about 1 second.

2. The process of claim 1 wherein the solids density is about 80 to about 200 kilograms per cubic meter.

3. The process of claim 1 wherein the superficial linear gas velocity is about 2.0 to about 4.5 meters per second.

4. The process of claim 1 wherein the solids feed rate is about 5 to about 250 kilograms per square meter per second.

5. The process of claim 1 wherein the residence time of the gases is about 0.1 to about 20 seconds.

6. The process of claim 1 wherein the residence time of the gases is about 1 to about 10 seconds.

7. The process of claim 1 wherein the reaction temperature is in the range of about 375° to about 525° C.

8. The process of claim 1 wherein the reaction temperature is in the range of about 450° to about 490° C.

9. The process of claim 1 wherein the ammoxidation catalyst contains antimony uranium and titanium, zirconium, hafnium or tin.

10. The process of claim 1 wherein the ammoxidation catalyst is defined by the formula $USb_2MO_{9-10}$, wherein M is Sn, Ti, Zr or Hf.

11. The process of claim 10 wherein the catalyst additionally contains silica.

12. The process of claim 1 wherein the reactor effluent is passed to a separator wherein the gaseous products and solids are separated from each other at a temperature about 25° C. to about 150° C. below the reaction temperature.

13. The process of claim 1 wherein the reactor effluent is passed to a separator, wherein the gaseous products and solids are separated from each other at a temperature about 40° to about 100° C. below the reaction temperature.

14. The process of claim 1 wherein the catalyst is separated from the reaction product and recycled to the reaction zone.

15. The process of claim 12 wherein the solids are recycled to the reaction zone.

16. The process of claim 13 wherein the solids are recycled to the reaction zone.

17. The process of claim 1 wherein the oxygen is added step-wise to the reaction zone.

* * * * *